United States Patent [19]
Lipsztajn

[11] Patent Number: 5,948,236
[45] Date of Patent: Sep. 7, 1999

[54] DETERMINATION OF CHLORATE ION CONCENTRATION USING MICROELECTRODES

[75] Inventor: Marek Lipsztajn, Etobicoke, Canada

[73] Assignee: Sterling Canada, Inc., Islington, Canada

[21] Appl. No.: 08/912,171

[22] Filed: Aug. 15, 1997

Related U.S. Application Data

[60] Provisional application No. 60/024,497, Aug. 22, 1996.

[51] Int. Cl.$^6$ .................................................. G01N 27/26
[52] U.S. Cl. ...................... 205/778.5; 204/400; 204/412; 205/780
[58] Field of Search .................................. 204/400, 402, 204/412; 205/778.5, 779, 779.5, 780

[56] References Cited

U.S. PATENT DOCUMENTS

| | | | |
|---|---|---|---|
| 4,028,197 | 6/1977 | Capuano | 205/780 |
| 5,437,772 | 8/1995 | De Castro et al. | 205/778.5 |

FOREIGN PATENT DOCUMENTS

216543 A1  12/1984  Germany.

OTHER PUBLICATIONS

Gifford et al, "Pneumatoamperometric Determination of Parts–per–Billion Dissolved Speries by Evoling Reactions", Analyticals Chemistry, vol. 25, No. 7, Jun. (1980), pp. 1024–1028.

Vogel's "Textbook of Quantitative Inorganic Analysis" Fourth edition 1978 month unavailable, pp. 363, 381, 493, 494.

"The Behavior of Microelectrodes" by S. Pons and M. Fleischmann, Analytical Chemistry, vol. 59, No. 24 (Dec. 15, 1987), pp. 1391A–1399A.

Primary Examiner—T. Tung
Attorney, Agent, or Firm—Sim & McBurney

[57] ABSTRACT

An in-situ procedure is described for measuring chlorate ion concentration in aqueous media containing the same by employing electrodes, particularly microelectrodes which generate a sigmoidal-type response at high chlorate ion concentration, and which exhibit catalytic properties toward chlorate ion electroreduction or electrooxidation.

12 Claims, 1 Drawing Sheet

DETERMINATION OF CHLORATE ION CONCENTRATION USING MICROELECTRODES

Provisional application of Ser. No. 60/024,497, filed Aug. 22, 1996.

FIELD OF INVENTION

The present invention relates to the determination of chlorate ion concentration in aqueous media.

BACKGROUND TO THE INVENTION

Chloric acid and corresponding salts, namely chlorates, especially alkali metal chlorates, are commonly used as raw materials in the pulp and paper industry, in particular in the generation of chlorine dioxide, which is used in the bleaching of pulp. Both in the chlorate manufacturing process and in the processes utilizing chlorate as a feedstock, there is a need to monitor the concentration of the chlorate ion on a periodic or, preferably, continuous basis. Numerous methods of chlorate ion determination are described in the literature (ref. 1, the references are listed at the end of the specification and their disclosures are incorporated herein by reference) but none of them can be applied for an in-situ determination of chlorate ion concentration, in particular at relatively high concentration levels characteristic for the processes related to the manufacture and applications of chlorate ions. The most commonly used method involves an ex-situ redox type multistep titration of a sample taken from a reactor, which requires pH adjustment, dilution and separation of other components of the analyte, such as chlorine dioxide, chlorine and chlorite, which may interfere with the titration method. A time delay between the moment of sampling and the end of the analysis does not permit a rapid response to process changes and, possibly, upset conditions, leading occasionally to unsafe situations.

There is a need, therefore, to develop an analytical method enabling an in-situ determination of chlorate ion concentration at the levels characteristic for processes including both the manufacture and utilization of alkali metal chlorates and chloric acid.

SUMMARY OF THE INVENTION

It has surprisingly been found that certain electrodes, preferably subjected to a specific pretreatment, became sensitive to chlorate ion concentration and generate an electrical signal proportional to the chlorate ion concentration. It was also found that the size of the electrode is critical as far as the in-situ determination of chlorate ion at high concentration levels is concerned.

Accordingly, in the present invention, there is provided a method of determining the concentration of chlorate ions in an aqueous medium, which comprises immersing in said aqueous medium an electrode, generating an electrical signal at the electrode in response to the concentration of chlorate ions in the aqueous medium, and determining the magnitude of the electrical signal as a measure of the concentration of chlorate ions in the aqueous medium.

Various electroanalytical techniques can be employed for the determination of chlorate ion concentration in accordance with the invention. These techniques are typically based on the measurement of the current or charge at electrodes polarized with a potential at which chlorate ion may undergo either reduction or oxidation, whereby such redox reaction involves either direct or indirect passage of current between the electrode and the chlorate ion.

GENERAL DESCRIPTION OF INVENTION

Figure 1:
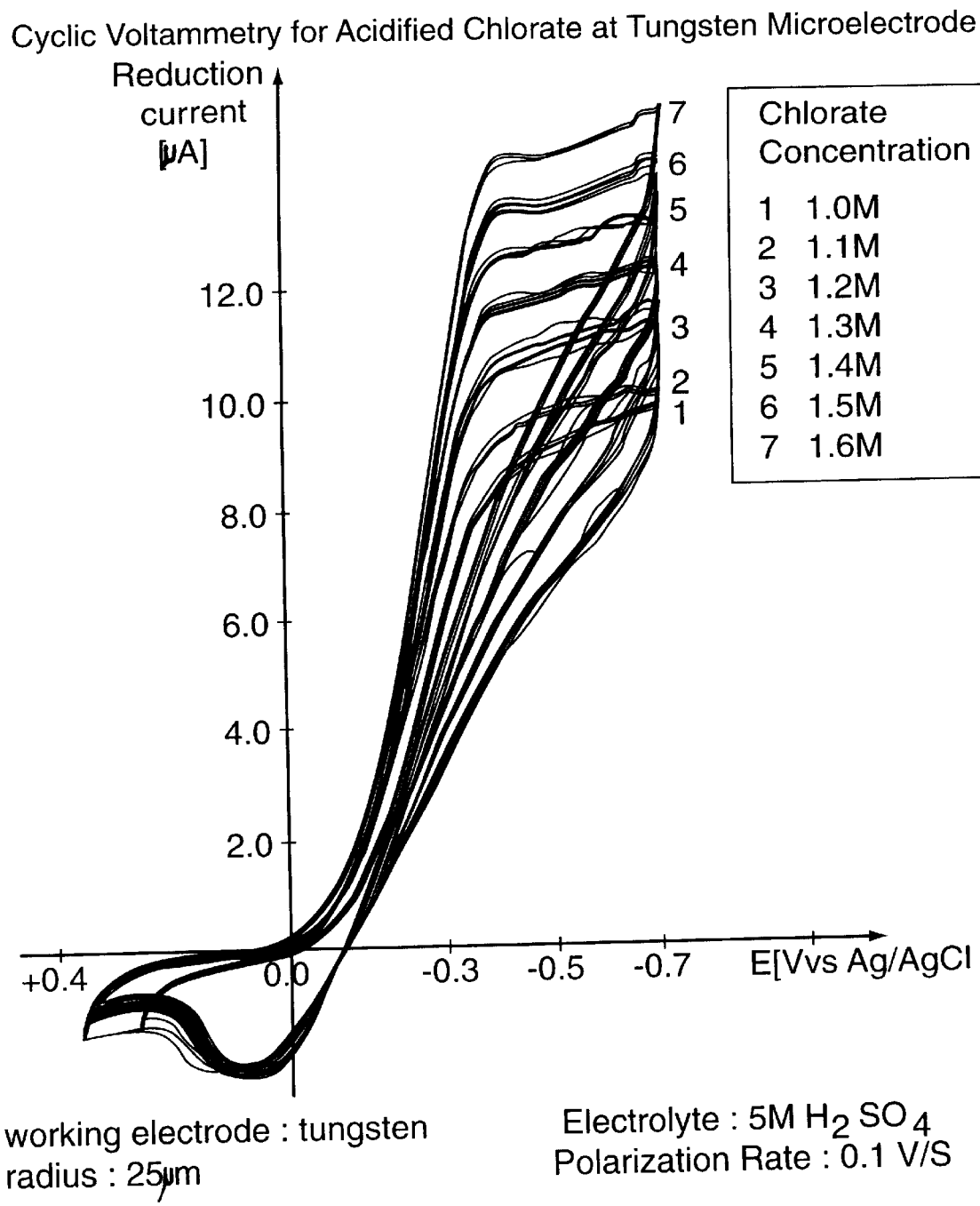
FIG. 1 is a graphical representation of scans from cyclic voltammetric experiments described below.

In the indirect type process, the actual redox reaction occurs between the intermediate species, formed, for example, by electrode material oxidation or reduction and the chlorate ions. It is believed that an appropriate pretreatment of the electrode leads to the presence of catalytic properties of such electrode.

Specific electroanalytical techniques may vary by the mode of the electrode polarization. Typically, techniques, such as single cycle voltammetry, cyclic voltammetry, continuous cyclic voltammetry (with and without the integration of current), square wave voltammetry, AC voltammetry, chronovoltamperometry, chronocoulometry, chronopotentiometry, as well as various potentiostatic and galvanostatic techniques can be employed. The working electrode may be stationary or rotating. A description of various electroanalytical techniques can be found in numerous textbooks, for example in ref. 2, the disclosure of which is incorporated herein by reference.

In order to measure a distinct signal proportional to chlorate ion concentration, it is beneficial to utilize electrodes at which the competing redox reactions, such as, for example, the hydrogen evolution reaction or oxygen evolution reaction, do not interfere. This can be achieved by employing electrodes characterized by sufficiently high overpotential towards the competing reactions and at the same time exhibiting catalytic properties towards the chlorate ion electroreduction or electrooxidation. Electrode materials that fulfil these requirements include, for example, tungsten, molybdenum, chromium, titanium, zirconium, niobium, tantalum, cadmium, lead, nickel, platinum, iridium, ruthenium, rhodium, osmium, palladium, as well as the corresponding compounds, for example, oxides and alloys as well as combinations thereof.

For the determination of chlorate ion concentration at the relatively high levels characteristic for the chlorate manufacturing process and the processes involving chlorate ion conversion to chlorine dioxide, it is important to size the electrodes appropriately. At the chlorate concentrations exceeding 0.1 M and, in particular, in the range of from about 0.5 M to about 6 M, it is critical to employ small size electrodes, often called microelectrodes. In contrast to conventional electrodes having a radius in the millimeter range, microelectrodes are much smaller, having a radius typically in the few tens micrometers range (<100 $\mu$m) or less, down to a few hundred angstroms.

A brief description of microelectrodes can be found, for example, in ref. 3, the disclosure of which is incorporated herein by reference. Conventional electrodes having a radius exceeding 100 $\mu$m can also be employed for chlorate ion determination, however, preferably only at lower concentration levels, typically less than about 0.1 M. In contrast, microelectrodes are applicable at any chlorate ion concentration, however, they are particularly useful at higher levels where the conventional size electrodes are not suitable, mainly due to the excessively high output signal and related high ohmic drop.

When employing various electroanalytical techniques to determine the concentration of chlorate ion herein, it is beneficial to obtain an output signal which is dependent only on chlorate ion concentration, but essentially independent of process conditions, such as electrode potential in a certain range, mixing, flow rate, conductivity, temperature, the presence of slurry or gases in the analyzed solution, other components of the analyte, etc. It is believed that smaller electrodes enable this objective to be achieved more readily, since they are better suited to generate a so-called sigmoidal type response, in which a plateau on the current vs. potential dependence is observed rather than a peak type response. Microelectrodes also enable an operation at very low currents, thus minimizing the ohmic drop in the analyzed solution.

The selection of the electrode material may be dependent on the specific process conditions, such as, for example, acidity. Chlorine dioxide generation processes involving chlorate ion reduction require typically highly acidic reaction media. In such a case, the long term stability of the electrode material, in particular its resistance towards corrosion, has to be considered. In acidic medium, microelectrodes made from tungsten, titanium, molybdenum, tantalum, chromium, zirconium, niobium, platinum, iridium, rhodium, ruthenium, palladium, osmium, lead, cadmium, as well as the corresponding compounds, for example, oxides, alloys and combinations thereof, can be employed.

At higher pH values, for example, in the neutral pH range characteristic for the chlorate manufacturing process, an electrode made from Raney nickel may be employed in addition to electrodes made from some of the materials listed above.

The electrochemical measurement effected herein is typically conducted in a three-electrode system (working electrode/counter electrode/reference electrode) or, possibly, a two-electrode system (working electrode/counter electrode). Standard reference and counter electrodes may be employed in such measurements.

When drastic changes of the composition of the analyzed solution are avoided, commercially available standard reference electrodes, such as calomel electrode or silver/silver chloride electrode, may be substituted for by an internal reference electrode, which may simply be a metallic wire, such as, a platinum wire. The area of the counter electrode may typically be larger than that of the measuring microelectrode.

As indicated earlier, the proper pretreatment of the chlorate sensing electrode is important. While it is possible to monitor the chlorate concentration by a continuous or periodic recording of a current or charge output from an electrode polarized with a constant potential, preferably corresponding to the plateau on the sigmoidal type response, it is beneficial to periodically polarize the electrode with a potential at which such electrode is preoxidized. Such a treatment is particularly useful when the chlorate ion determination is based on the cathodic reduction of chlorate ion. The preoxidation in such a case can be achieved by imposing a potential less negative than that at which the actual cathodic measurement of chlorate concentration takes place. The scanning of the electrode between the "chlorate determination potential" and the "pretreatment potential" can be achieved manually or automatically using standard electronic equipment available for various electroanalytical techniques. Such a scanning can be continuous of the type typically employed in the cyclic voltammetry or may involve various pulse techniques with electrode potential being switched between two or more specific values for a set period of time.

It is believed that, at the concentration ratios of chlorate to other electroactive species typically present in the chlorine dioxide generators and in the chlorate manufacturing process, the current output of chlorate sensing microelectrodes is primarily related to the chlorate ion concentration with essentially no interference from other species.

The acidity may have some influence on the current response, for example, on the width and the position of the plateau. In fact, from the chlorate measurement and some other data describing the operation of the chlorine dioxide generator, such as, for example, the boiling point of the generator liquor, conclusions concerning the acidity can be drawn. A manual or, preferably, computerized system may allow instantaneous information to be obtained about the acidity of the generator liquor based on the chlorate measurement output.

The composition of analysed solution, for example, the concentration of sulfate ions and the degree of saturation may have some effect on the measurement, since the composition affects, for example, the diffusion coefficient of chlorate ions and the viscosity of the solution as well as the free acidity. In fact, the chlorate ion measurement may be used to estimate the free acidity of the analysed solution.

Alternatively to continuous, on-line measurement, an ex-situ analysis can be effected by withdrawing a sample from the analysed stream and then measuring the chlorate concentration of the sample. Optionally, the composition of the sample may be adjusted by, for example, adding sulfuric acid. The latter approach may be particularly useful when dealing with highly-saturated solutions.

While the method described above is applicable specifically to the in-situ determination of chlorate ion concentration at higher levels, a similar approach can be taken in quantitative analysis of related species, such as, for example, chlorite, chlorine dioxide, chloride, hypochlorite and perchlorate.

In fact, the novel concept of employing microelectrodes for an on-line determination of high concentrations in solutions can be extended to many other electroactive species. There are numerous examples of analytical methods based on electroanalytical techniques applicable only in dilute streams which can be modified to accommodate more concentrated streams using the novel approach based on microelectrodes.

EXAMPLE

Cyclic voltammetric measurement was conducted in a three-electrode system comprising a chlorate sensing microelectrode made from tungsten (a disk of the radius 25 $\mu$m), a counter electrode made from graphite and a silver/silver chloride reference electrode. The analyzed solution contained initially 5 M $H_2SO_4$ and 1 M $NaClO_3$ as well as small quantities (less than 1 gpL) of chlorine dioxide and chlorine.

A cyclic voltammetric potential scan at the rate of 0.1 V/sec was applied continuously between the limits of +0.4 V and −0.7 V vs. Ag/AgCl.

A nearly sigmoidal current response with a plateau between −0.4 V and −0.7 V vs. Ag/AgCl was observed. As shown in FIG. 1, the consecutive scans resulted in a very similar current response, indicating a very good reproducibility of the measurement.

Subsequently, several incremental additions of concentrated (6 M) sodium chlorate were made to the same analyte, resulting in the final chlorate ion concentrations of 1.1 M, 1.2 M, 1.3 M, 1.4 M, 1.5 M and 1.6 M. The current response was found to be linearly dependent on chlorate concentration. Reproducibility was very good for all the runs.

There was no apparent interference from other electroactive species present in the analyte, such as chlorine dioxide or chlorine.

SUMMARY OF THE DISCLOSURE

In summary of this disclosure, the present invention provides a novel in-situ procedure for measuring chlorate ion concentration in aqueous media containing the same, such as during the production of chlorine dioxide or during the electrochemical production of an alkali metal chlorate, by employing an electrode, preferably a microelectrode which exhibits catalytic properties towards chlorate ion electroreduction or electrooxidation, so that the redox reaction involves either direct or indirect passage of current between the electrode and the chlorate ion. The electrode preferably has a high overpotential for competing reactions. Modifications are possible within the scope of this invention.

What I claim is:

1. A method of determining the concentration of chlorate ions in an aqueous medium having a chlorate ion concentration of at least about 0.1 M, which comprises:

immersing in said aqueous medium a microelectrode having a major dimension of less than about 100 $\mu$m, generating an electrical signal at the microelectrode in response to the concentration of chlorate ions in the aqueous medium, and determining the magnitude of the electrical signal as a measure of the concentration of chlorate ions in the aqueous medium.

2. The method of claim 1 wherein said microelectrode is polarized with a potential at which chlorate ion undergoes either reduction or oxidation, whereby a redox reaction involves passage of current between the electrode and the chlorate ion.

3. The method of claim 2 wherein the redox reaction occurs between intermediate species formed by microelectrode oxidation or reduction and the chlorate ions.

4. The method of claim 1 wherein said microelectrode exhibits a high overpotential towards reactions competing with electroreduction or electrooxidation of chlorate ions while catalytic towards the electroreduction or electroxidation reactions.

5. The method of claim 4 wherein said microelectrode is constructed of a material selected from the group consisting of tungsten, molybdenum, chromium, titanium, zirconium, niobium, tantalum, cadmium, lead, nickel, platinum, iridium, ruthenium, rhodium, osmium, palladium, oxides of such metals, alloys of such metals and combinations of such metals.

6. The method of claim 1 wherein said chlorate ion concentration is about 0.5 to about 6 M.

7. The method of claim 1 wherein said electrical signal has a magnitude dependent solely on chlorate ion concentration and independent of other process condition.

8. The method of claim 1 wherein the chlorate ion concentration of the aqueous medium is monitored and a current or charge output from the microelectrode polarized with a constant potential is recorded.

9. The method of claim 8 wherein said microelectrode is polarized with a potential corresponding to a plateau or a sigmoidal type response.

10. The method of claim 1, wherein the microelectrode is periodically polarized with a potential at which the electrode is preoxidized.

11. The method of claim 1 wherein the chlorate concentration is determined in a three-electrode system comprising the microelectrode as a working electrode, a counter electrode and a reference electrode.

12. The method of claim 1 wherein cyclic voltammetric measurement is used to monitor the concentration of chlorate ions in the aqueous medium.

* * * * *